US012332229B2

(12) United States Patent
Hagen et al.

(10) Patent No.: US 12,332,229 B2
(45) Date of Patent: Jun. 17, 2025

(54) CALIBRATING A PLURALITY OF SENSORS IN A SYSTEM FOR OBTAINING ANIMAL DATA FROM A GROUP OF ANIMALS

(71) Applicant: Nedap N.V., Groenlo (NL)

(72) Inventors: Jorrit Hendrik Johan Hagen, Hengelo (NL); Rudie Jan Hendrik Lammers, Eibergen (NL); Arnoldus Gerardus Franciscus Harbers, Groenlo (NL)

(73) Assignee: Nedap N.V., Groenlo (NL)

( * ) Notice: Subject to any disclaimer, the term of this patent is extended or adjusted under 35 U.S.C. 154(b) by 688 days.

(21) Appl. No.: 17/675,871

(22) Filed: Feb. 18, 2022

(65) Prior Publication Data

US 2022/0283136 A1 Sep. 8, 2022

(30) Foreign Application Priority Data

Mar. 3, 2021 (NL) .................................... 2027684

(51) Int. Cl.
  *G01N 33/06* (2006.01)
  *A01J 5/01* (2006.01)
  *A01J 5/013* (2006.01)

(52) U.S. Cl.
  CPC ............... *G01N 33/06* (2013.01); *A01J 5/01* (2013.01); *A01J 5/0132* (2013.01)

(58) Field of Classification Search
  None
  See application file for complete search history.

(56) References Cited

U.S. PATENT DOCUMENTS

| | | |
|---|---|---|
| 2018/0279582 A1 | 10/2018 | Yajima et al. |
| 2020/0296935 A1 | 9/2020 | Ashek et al. |
| 2020/0305388 A1 | 10/2020 | Halachmi et al. |
| 2022/0003581 A1* | 1/2022 | Fox ........................ G01D 3/022 |
| 2022/0253781 A1* | 8/2022 | Pan .................. G06Q 10/06375 |

FOREIGN PATENT DOCUMENTS

| | | |
|---|---|---|
| WO | WO 2016/099293 A1 | 6/2016 |
| WO | WO-2018229142 A1 * | 12/2018 ........... A01K 1/0151 |

OTHER PUBLICATIONS

European Patent Office, Search Report and Written Opinion in corresponding Dutch Application No. 2027684 dated Nov. 19, 2021 (11 pages).

* cited by examiner

*Primary Examiner* — Suman K Nath
(74) *Attorney, Agent, or Firm* — Leydig, Voit & Mayer, Ltd.

(57) ABSTRACT

A method of calibrating a sensors in a system for obtaining animal data from animals is described. The sensors are configured to obtain measurements of an animal related parameter during arbitrary visits by the animal to the sensors. For at least one of the animals, a first measurement associated with a first sensor of the sensors is obtained, and calculating one or more relations between the first measurement and one or more second measurements associated with the respective animal. Each of the second measurements is obtained using a further sensor, so as to obtain at least one representative relation for each combination of the first sensor and each one of the further sensors. The system calculates, based on the at least one representative relation, a correction factor associated with at least one sensor of the plurality of sensors.

26 Claims, 5 Drawing Sheets

CALIBRATING A PLURALITY OF SENSORS IN A SYSTEM FOR OBTAINING ANIMAL DATA FROM A GROUP OF ANIMALS

CROSS-REFERENCE TO RELATED APPLICATIONS

This patent application claims priority to Netherlands Application No. 2027684, filed Mar. 3, 2021, the contents of which are expressly incorporated by reference in their entirety, including any references contained therein.

TECHNICAL FIELD AND BACKGROUND

The present invention is directed at a method of calibrating a plurality of sensors in a system for obtaining animal data from a group of animals, wherein the sensors are configured to obtain measurements of an animal related parameter, wherein for obtaining the measurements the system is configured for allowing each animal to arbitrarily visit one of the sensors. The invention is further directed at a computer program product.

Farm management systems typically include a variety of systems and devices for monitoring the health, wellbeing and productivity of the animals present on a farm. Typically, on a dairy farm, a milking system is present to enable the dairy cattle to be milked e.g. twice a day. As another example, weighing systems may be used comprising a plurality of weighing stations for monitoring the weight of individual animals, for example on a dairy farm, pig farm, breeding farm or meat production farm. Various other examples may be thought of, such as feeding systems, watering systems or infrared based temperature monitoring systems, which may be applied to monitor groups of animals.

Although the above systems have made farming of groups of animals more easy and less labor intensive, a downside of these systems is the individual sensors need to be calibrated frequently for a variety of reasons. For example, wear of the sensors caused by frequent use thereof typically requires frequent recalibration of each sensor. Also, not every sensor is used with a same frequency. Some sensors are more popular, for example due to a convenient placement, while other sensors may not be used very often because the animals may have access to it only occasionally. Also, environmental conditions may differ from sensor to sensor, resulting in some sensors requiring recalibration more often than other sensors. Calibration of a large number of sensors is a labor intensive task, and typically requires each sensor to be calibrated individually.

SUMMARY OF THE INVENTION

It is an object of the present invention to provide an efficient method of calibrating a plurality of sensors in a system as described above, which may be performed frequently without too much effort.

To this end, there is provided herewith a method as described above, wherein the method comprises: obtaining, for at least one animal of the group of animals, a first measurement associated with a first sensor of the plurality of sensors; calculating one or more relations between the first measurement and one or more second measurements associated with the respective animal, wherein each of the second measurements is obtained using further sensor different from the first sensor, such as to obtain at least one representative relation for each combination of the first sensor and each one of the further sensors; and calculate, based on the at least one representative relation, a correction parameter associated with at least one sensor of the plurality of sensors, for harmonizing an output signal of the at least one sensor with respect to output signals of one or more further sensors of the plurality of sensors. The correction parameter may be a correction factor or an offset. In the present document, in many occasions reference is made to a 'correction factor' whereas the same teaching likewise applies to the calculation of offset values. For example, where offset values are known the correction factors may be accurately determined in the manner described, and where correction factors are known it is possible to determine the offset values.

The invention is based on the insight that the measurements of an animal related parameter associated with a same animal in many cases are related in the sense that they follow a predictable trend (such as animal weights) or are more or less constant (such as milk yield per milking session or per twenty-four-hour-period) for a given time period. Therefore, by acquiring measurements associated with an individual animal that were obtained via different sensors, the relations between these measurements provide information about how the errors in the measurement signals from two sensors in a sensor combination relate to each other. For example, it may be assumed that two measurements of weight of an animal taken within a time frame of a few days are based on the real weight of the animal (which is constant (except for small differences due to feeding)), and thus the ratio or fraction between these two measurements provides information about how the same quantity is measured by the two different sensors. Thus, by combining measurements from a certain sensor with those of all other sensors in sensor pairs or sensor combinations, it is possible to perform a calibration of the whole system. This may in a most basic form be done by harmonizing the outputs of all sensors based on the determined relations. In that case, the sensor outputs of all sensors are compensated based on the relations such that the reading of each sensor are comparable and do not comprise a mutual difference. In a more accurate implementation, either at least one of the sensors is well calibrated or its correction factor is well known, or one or more reference measurements are performed. In principle, if reference measurements are performed, a single reference measurement may already be sufficient.

In preferred embodiments, the step of calculating one or more relations between the first measurement and one or more second measurements comprises calculating one or more fractions between the first measurement and one or more second measurements, such as to obtain at least one representative fraction for each combination of the first sensor and each one of the further sensors. From the fractions, and optionally by including reference measurements, correction factors for compensating sensor values can be calculated. Consider, for example, a parameter that can be assumed constant during two or more subsequent measurements. Any trend information may in that case, for the present example, be disregarded. Assume further that the sensor data is already corrected for offset values (determinable for each sensor by performing a benchmark or baseline measurement). In mathematic form, the above principle for each combination of sensors may then be expressed as follows:

$$\delta_1/\delta_2 = f_2/f_1$$

wherein $\delta_1$ and $\delta_2$ are measurement values obtained with respectively a first and second sensor, and wherein $f_1$ is the correction factor of the first sensor and $f_2$ is the correction factor of the second sensor. The fraction $\delta_1/\delta_2$ thus enables to calculate $f_2$, if $f_1$ can be found in another manner e.g. using a reference measurement. For example, if $\delta_{real}$ is the actual value of the animal related parameter to be determined, then $f_1=\delta_{real}/\delta_1$, wherein $\delta_1$ is the sensor reading of the first sensor. With this information also $f_2$ can be calculated.

In some embodiments, the second measurements are obtained from a data repository containing measurement data of earlier measurements, wherein in the measurement data each measurement is associated with an animal identifier of an animal from the group of animals, and wherein in the measurement data each measurement is associated with a sensor identifier of the sensor with which the measurement has been obtained. For example, a farm management system may store milking data of the milk yield for a number of days or weeks, and from this the measurement data required for carrying out the calibration method may be acquired. As may be appreciated, sensor combinations or sensor pairs may be formed based on data from one animal; however the relations obtained therefrom are no longer specifically related to the animal but merely to the sensors of the pair. Furthermore, where the relations are fractions, the fraction of a sensor A with respect to a sensor B is the inverse of the fraction of sensor B with respect to sensor A. The fraction of a sensor with respect to itself is by definition equal to 1. To calculate relations, historic measurement data can thus be used of different animals, provided that for calculating a single relation of a population of relations for a certain sensor pair or sensor combination the measurement data of a same animal must be used. The calibration may be performed using the latest data compared to the data of the days or weeks before. However, using the memory or data repository, a calibration may also be performed on historic data in the past (provided that also a reference measurement for this historic data can be provided), if needed.

In some embodiments, the first measurement is obtained from a data repository containing measurement data of earlier measurements. However, the first measurement may also be obtained directly from the first sensor on the day the measurement is performed. Furthermore, in some embodiments, the one or more second measurements include at least one measurement from each of the sensors different from the first sensor. In other embodiments, the one or more second measurements include a plurality of measurements from one or more or each of the further sensors, wherein the step of calculating one or more relations is performed by calculating relations between the first measurement and a statistical representative value of the plurality of measurements for each of the further sensors. For example, the statistical representative value may be at least one of: an average; a median value; a mode; or a percentile of the plurality of measurements of the further sensor. Additionally, it is also possible to filter out outliers or only take into account those measurements which are within two or three standard deviations from the mode or average.

In some embodiments, for obtaining the at least one representative relation for each combination of the first sensor and each one of the further sensors, the method further comprises: after the step of calculating one or more relations, storing each of the calculated relations in a data repository; and selecting from the data repository, for each combination, a plurality of stored relations and calculating the representative relation from the selected relations. Although a single calculated relation may be sufficient in some embodiments, the representative relation may be obtained from a number of calculated relations, e.g. 5, 10, 20, 50, 100, 200 or 500 relations or an average, median, mode, or percentile of all relations for a combination. As may be appreciated, the above may be combined where necessary with rounding or similar, normal correction of sensor values.

In some embodiments, the method may further include a step of modifying one or more representative relations of the set containing the representative relations of each combination of the first sensor and each one of the further sensors, the modifying including correcting the said one or more representative relations such as to bring the representative relations in conformity with each other. It may be the case that, after collecting all the representative relations, an inconsistency still remains amongst these. In this case, a step of increasing the consistency of the values will improve the representative relations as a whole and improve the quality of the results obtained.

As already mentioned above, in some preferred embodiments, the method further comprises a step of: obtaining a reference measurement of the at least one animal related parameter using at least one sensor of the plurality of sensors; and in addition to the at least one representative relation, the correction factor is calculated based on the reference measurement. The system may be automatically well calibrated, with respect to all sensors, with the use of at least one reference measurement to which all other measurements can be related.

In some embodiments, the reference measurement comprises one or more measurements of the at least one animal related parameter obtained using a reference sensor, wherein at least one of: the reference sensor is an arbitrary sensor of the plurality of sensors; or the reference sensor is a calibrated sensor. In principle, because the representative relations of each sensor pair or sensor combination is now available, a calibration may be performed on the basis of a single reference measurement. From this, corrections factors for all sensors can be calculated. The reference measurement may be obtained from an arbitrary sensor of the system, which may be a calibrated sensor or not. In the latter, where an arbitrary uncalibrated sensor would be used, the method at least enables to harmonize the measurements obtained from all sensors (e.g. such that they are directly comparable to each other) regardless of a potential error therein. If a calibrated sensor is used, which could be any of the regular sensors or a specially added calibrated sensor, the output from this sensor enables to provide a more reliable value based on which the other correction factors may be determined. In one embodiment, the method therefore further comprises calculating, for the reference sensor, a correction factor based on the reference measurement and a calibrated value, wherein the calibrated value is a representative value for the at least one animal related parameter; and calculating, based on the correction factor of the reference sensor and said at least one relation for each combination of the first sensor and each one of the further sensors, further correction factors, such as to obtain correction factors for each sensor of the plurality of sensors.

As explained herein before, where the relations are fractions, by combining measurements for a specific animal obtained with a certain sensor with measurements for that animal obtained with all other sensors in sensor pairs or sensor combinations, fractions can be calculated that equal the inverse fraction between the correction factors of these sensor pairs (without knowing yet the actual correction factors $f_i$). Thus for a first and second sensor in a combination, it is possible to write: $\delta_1/\delta_2=f_2/f_1$, wherein $\delta_1$ and $\delta_2$ are measurement values obtained with respectively a first and second sensor, and wherein $f_1$ is the correction factor of the first sensor and $f_2$ is the correction factor of the second sensor. The fraction $\delta_1/\delta_2$ thus enables to calculate $f_2$, if $f_1$ can be found in another manner e.g. using a reference measurement. If $\delta_{real}$ is the actual value of the animal related parameter to be determined, then $f_1=\delta_{real}/\delta_1$, wherein $\delta_1$ is the sensor reading of the first sensor. With this information also $f_2$ can be calculated. Now, for example, suppose the sensor readings relate to the weight of a specific pig within a group of pigs, then the weight of the pig may first be measured using an accurate calibrated scales to determine the real weight ($\delta_{real}$) at time $t_0$. Thereafter, the pig may be placed in the environment wherein the weighing system is installed and each weighing unit may send the determined weight data and identification data of the pig to a controller, which stores the data including an identifier for the weighing unit in a memory or database. After a few days, at the end of the calibration period, the pig may have visited all weighing units and the memory is filled with a sufficient amount of measurements. Fractions may then be calculated for each combination of sensors. A single measurement of one of the sensors, e.g. the weight data ($\delta_1$) of the first measurement by a weighing unit that is visited after to, enables to calculate the correction factor for that weighing unit using $\delta_{real}$ and $\delta_1$ by $f_1=\delta_{real}/\delta_1$. Once $f_1$ is known, the other correction factors of the other weighing units can be calculated. Optionally, at the end of the calibration period, a new reference measurement may additionally be performed using the accurate calibrated scales to determine the real weight ($\delta_{real}$) at time $t_1$. The two measurements of $\delta_{real}$ at times $t_0$ and $t_1$ can be used to derive trend data, and to compensate the weight measurements of the other sensors based on the trend data. Therefore, in accordance with some embodiments, the first measurements and the one or more second measurements are obtained within a predefined time period, such that within said time period the obtained measurements of the animal related parameter are correlated in accordance with a data trend.

Therefore, in some embodiments, the first measurement is obtained at a first moment of time and the second measurement is obtained at a second moment of time, wherein prior to performing the step of calculating the one or more relations between the first measurement and one or more second measurements, the method may include dividing the first measurement by a first calculated estimate and dividing the second measurement by a second calculated estimate, wherein the first and the second calculated estimates are determined based on the data trend. For example, the data trend is determined based on measurements performed using one or more sensors of the plurality of sensors.

Where the animal related parameter may follow a certain (known or unknown) trend, fractions may likewise be used as the abovementioned calculated relations, and these fractions may relate as follows: $[\delta_1/h(t_1)]/[\delta_2/h(t_2)]=f_2/f_1$ wherein $\delta_1$ and $\delta_2$ are measurement values obtained with respectively a first and second sensor, and wherein $f_1$ is the correction factor of the first sensor and $f_2$ is the correction factor of the second sensor. Here h(t) is the true value as a function of time.

If g(t) denotes a statistically representative measured trend value as a function of time based on how randomly all animals visit the sensors, then it may be assumed that $h(t) \approx g(t)*<f>$, where $<f>$ is a statistically representative correction factor for the entire embodiment. Then: $[\delta_1/\{g(t_1)*<f>\}]/[\delta_2/\{g(t_2)*<f>\}] \approx f_2/f_1$, and thus: $[\delta_1/g(t_1)]/[\delta_2/g(t_2)] \approx f_2/f_1$. Thus the ratio of measurement $\delta_1$ corrected for its associated measured trend value with respect to measurement $\delta_2$ corrected for its associated measured trend value will give an estimate for $f_2/f_1$. Repeating such measurement will enable to compute a more statistically representative value for $f_2/f_1$.

In a specific class of embodiments, the method is applied is to a milking system on a dairy farm. In accordance with these embodiments, the system for obtaining animal data from a group of animals is a milking system for milking animals of the group of animals, the animals being dairy animals, wherein the sensors of the plurality of sensors comprise at least one element of a group comprising: milk meters wherein the measurements comprise measurements of quantities of milk obtained from each of the animals; conductivity sensors for determining a conductivity of the milk obtained, color meters for determining a color of the milk obtained, fat percentage sensors, protein sensors for determining a specific amount of protein in the milk obtained, cell count sensor for determining a somatic cell count of the milk, lactose sensor for determining a lactose level of the milk.

For example, in some of these embodiments, the sensors of the plurality of sensors comprise milk meters wherein the measurements comprise measurements of quantities of milk obtained from each of the animals, and the system comprises N milk meters, and wherein the step of obtaining the reference measurement comprises: obtaining a total milk yield D from all milk meters in the system during at least one complete milking session; obtaining a sensor milk yield $d_i$ representative of a total milk yield of an $i^{th}$ milk meter during the at least one complete milking session, wherein $1 \leq i \leq N$ and $i \in \mathbb{N}$; calculating a system correction factor $f_{system}$ as:

$$f_{system} = \frac{D}{\sum_{i=1}^{N} d_i};$$

and
wherein the step of calculating the correction factor for a $j^{th}$ milk meter (wherein $1 \leq j \leq N$ and $j \in \mathbb{N}$ and $j \neq i$), comprises calculating $f_j$ as:

$$f_j = f_{system} \times \frac{\sum_{i}^{N} d_i}{\sum_{i}^{N} \left[d_i\left(\frac{f_i}{f_j}\right)\right]}.$$

In the above, the total milk yield D could be a calibrated value, e.g. based on a bulk tank measurement and/or using a calibrated sensor.

In accordance with the above embodiments, the sensors are milk meters of a milking system. The milk yield of a dairy animal, e.g. a cow, a goat or a sheep, is typically more or less constant over the period of a few weeks. Therefore, measurements of milk yield over a period wherein milking sessions are performed on a regular basis (say twice a day: at 8 am and 8 pm), are expected to be constant per animal (except for unforeseen circumstances, such as a malfunctioning milk meter or an exceptional health status). To find a calibrated value ($\delta_{real}$) in this case, a known quantity of milk may be provided to the milk meter or alternatively the real quantity of milk measured by that milk meter during a milking session at least of one specific cow may be determined separately using an accurate calibration measurement. Similar to the above weighing system, this can be used to calculate the correction factor of that particular milk meter, which in combination with the relations obtained for all sensor combinations may be used to find the other correction factors of the other sensors.

However, alternatively, another way to find a calibrated value in this case is to perform a complete normal milking session (as it is done twice a day), and determine the total milk yield D from that session over all cows and all milk meters. This value may be determined by measuring the total milk yield based on a bulk tank measurement. Suppose there is a total number of K cows in a group of animals and the system includes N milk meters and that $K_i$ animals visit the $i^{th}$ sensor. Let $d_i$ denote the total measured yield of the $i^{th}$ sensor for all cows that have visited the sensor (i∈ N and $1 \leq i \leq K_i$), which in turn can be calculated as:

$$d_i = \Sigma_{k=1}^{Ki} \delta_{ik}$$

wherein $\delta_{ik}$ is the measured yield determined with the $i^{th}$ sensor for cow k, where k denotes each cow in the group at the $i^{th}$ sensor (k∈ N and $1 \leq k \leq K_i$). From this, the correction factor for the whole system $f_{system}$ can be calculated as:

$$f_{system} = \frac{D}{\sum_{i=1}^{N} d_i}$$

This can be used to calculate the individual correction factor of a $j^{th}$ sensor (wherein j≠i, j∈ N and $1 \leq j \leq N$) using the fractions $f_i/f_j$ as follows:

$$f_j = f_{system} \times \frac{\sum_{i}^{N} d_i}{\sum_{i}^{N}\left[d_i\left(\frac{f_i}{f_j}\right)\right]}$$

Note hereby that the fractions $f_i/f_j$ are obtained as described above. The above may also be performed over multiple milking sessions in a similar way by summing all milk yields and parallel thereto determining the total milk yield obtained from these sessions.

In a further specific class of embodiments, the method may be applied to a weighing system on a farm. Here, the system for obtaining animal data from a group of animals is a weighing system, wherein the sensors of the plurality of sensors are weighing units, and wherein the measurements comprise measurements of weights of individual animals from the group of animals.

In some of the above embodiments, the method further comprises a step of obtaining a reference measurement of the at least one animal related parameter using at least one sensor of the plurality of sensors, and wherein in addition to the at least one representative relation, the correction factor is calculated based on the reference measurement, wherein the reference measurement comprises at least one of: an average weight of an individual animal obtained by averaging measurements of weights of the respective animal obtained using at least a subset of the sensors, including at least two of the sensors; or a reference measurement of the weight of an individual animal using a calibrated weighing unit.

In yet a further specific class of embodiments, the method may be applied to a feeding system. Here, the system for obtaining animal data from a group of animals is a feeding system comprising one or more feeding stations, wherein the sensors of the plurality of sensors are weighing units for determining a quantity of feed, and wherein the measurements comprise measurements of quantities of feed consumed by individual animals from the group of animals.

In yet a further specific class of embodiments, the method may be applied to a measuring system wherein the sensors of the plurality of sensors are configured for measuring animal related parameters including at least one element of a group comprising: temperature; color; size such as height, width or length; mobility or behavioral parameters. In general the measuring system in accordance with this class of embodiments may be configured for measuring any parameters that can be measured outside an animal. Size related parameters may for example be obtained by a 3D camera system. Such a 3D camera system may be installed at different angles and for that reason may need to be corrected.

In accordance with a further aspect of the present invention, there is provided a computer program product for use in a system for obtaining animal data from a group of animals, for calibrating a plurality of sensors of the system, wherein the sensors are configured to obtain measurements of an animal related parameter, wherein for obtaining the measurements the system is configured for allowing each animal to arbitrary visit one of the sensors, wherein the system at least comprises a controller, the computer program product including instructions for causing the controller to perform the steps of: obtaining, for at least one animal of the group of animals, a first measurement associated with a first sensor of the plurality of sensors; calculating one or more relations between the first measurement and one or more second measurements associated with the respective animal, wherein each of the second measurements is obtained using further sensor different from the first sensor, such as to obtain at least one representative relation for each combination of the first sensor and each one of the further sensors; obtain a reference measurement of the at least one animal related parameter using at least one sensor of the plurality of sensors; and calculate, based on the reference measurement and the at least one representative relation, a correction factor associated with at least one sensor of the plurality of sensors, for harmonizing an output signal of the at least one sensor with respect to output signals of one or more further sensors of the plurality of sensors. The computer program product may be stored on a data carrier or may be made available via an online data repository, such as to be downloaded via a wide area network. In particular, the computer program product may be configured such that when loaded into a memory of a farm management system, a milking system, a feeding or watering system or a weighing system, the instructions enable a controller of the system to perform the method of the present invention.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

DETAILED DESCRIPTION

In the below described embodiments, unless explicitly stated differently, the calculated relations will be referred to as fractions, in accordance with the preferred embodiments. The invention, however, is not limited to fractions only. Furthermore, the correction parameter referred to in this document may be a correction factor or an offset. In the present document, in many occasions reference is made to a 'correction factor' whereas the same teaching likewise applies to the calculation of offset values. For example, where offset values are known the correction factors may be accurately determined in the manner described, and where correction factors are known it is possible to determine the offset values. If both are to be determined, it is possible to apply the present invention in combination with a fitting method to determine both the offsets and correction factors.

Figure 1:
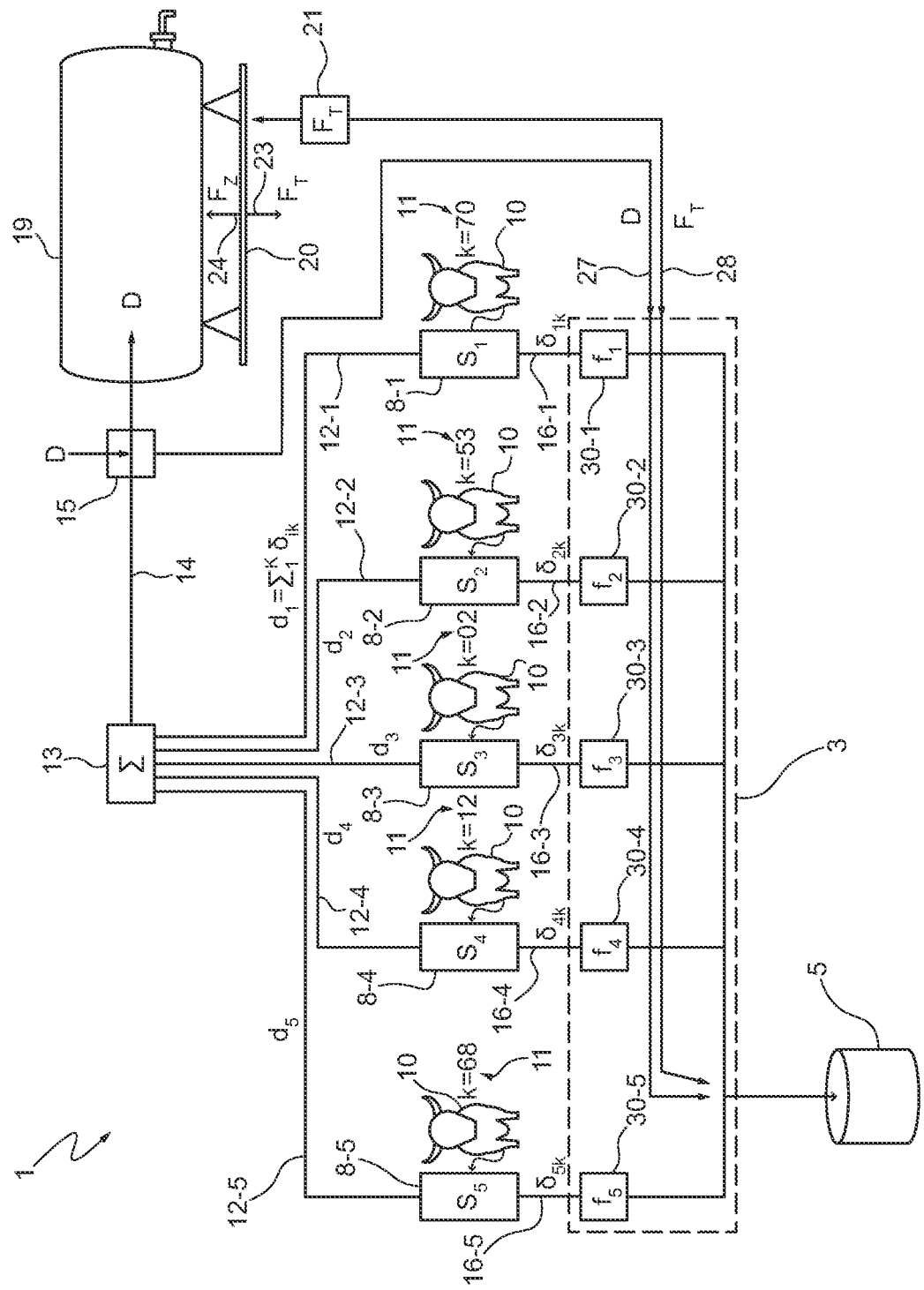
FIG. 1 schematically illustrates a milking system in accordance with an embodiment of the present invention, applying a method in accordance with an embodiment.

FIG. 1 schematically illustrates a milking system 1 in accordance with an embodiment of the present invention. The milking system 1 is illustrated schematically in order to visualize the transportation of milk and the data communication between the different elements of the system 1. The milking system 1 includes a controller 3 and memory 5. The controller 3 controls various processes of the milking system, amongst which is the data handling of measurement data obtained from the various sensors in the system 1. The milking system 1 comprises a plurality of milking units, including milk meters 8-1, 8-2, 8-3, 8-4 and 8-5 serving as sensors $S_1$ to $S_5$ that enable to measure the milk yield for each individual cow 10. Each of the cows 10 of a group of seventy cows may, during a milking session, arbitrarily visit one of the sensors $S_1$ through $S_5$ (milk meters 8-1 through 8-5). Each of the cows 10 has been assigned an identifier 11. The identifier 11, denoted as k, is an integer number between 1 and K, wherein K=70 for representing the group of seventy cows.

Each of the sensors 8-1 through 8-5 is part of a milking device which obtains milk from the cows 10 that visit the milking device. Milk transportation lines 12-1, 12-2, 12-3, 12-4 and 12-5 convey the quantities of milk obtained from all cows that have visited the respective milking devices. The milk from transportation lines 12-1 to 12-5 is collected in element 13 and conveyed via milk line 14 towards a storage tank 19, which will be unloaded regularly for further handling and processing. Upstream of the storage tank 19, a calibrated and accurate milk flow sensor or calibrated milk meter 15 determines the total quantity of milk D passing through in milk line 14 towards the storage tank 19. The total quantity of milk D measured by milk flow meter 15 includes all the individual milk quantities obtained from the various milking devices wherein the sensors 8-1 through 8-5 are installed, and from all cows 10 milked during that session. The aggregate value D is provided as a data signal to controller 3.

Merely as an example, suppose that the cows 10 are milked several times per day, e.g. typically twice a day, for example once at 8 am and once at 8 pm. As may be appreciated, if the cows 10 are milked twice per day, the cows 10 will over a period of a week be milked fourteen times. Ideally, if each cow 10 will individually visit a different sensor 8 during each milking session, then with five milk meter sensors 8 (8-1 through 8-5) each cow on average will visit each sensor 8 approximately three times over a full week. Since there are seventy cows which are milked twice a day for seven days, this will provide a total of approximately a thousand sensor readings. For five sensors 8-1 to 8-5 this will be approximately 200 readings per sensor. The sensor readings may be stored in memory 5 and be used for calculating the correction factors $f_1$ to $f_5$ of each sensor 8-1 to 8-5, as will be explained further below. As may be appreciated, the number of readings per sensor 8-1 to 8-5 in this example is largely dependent on the number of cows 10, the number of sensors 8, the number of milkings per day, and the number of days considered (here seven). The above example illustrates that over the course of just seven days, sufficient sensor readings may be obtained for any farm of any size to enable to perform the automatic sensor calibration method of the present invention. Of course, the invention may be applied in very different situations with different measurement frequencies using different numbers of sensors for different numbers of animals. For example, a weighing system for pigs on a breeding farm of approximately 1000 pigs, including 50 weighing stations, wherein the pigs visit an arbitrary weighing station e.g. 6 times per day.

The sensor readings for each individual cow 10 during a session are communicated by each of the milk meters 8-1 to 8-5, via each corresponding signal line 16-1 through 16-5, to the controller 3. The controller 3 will multiply each of the received milking yields δ for the specific cow 10 being milked, with a correction factor $f_1$ through f5, the elements 30-1, 30-2, 30-3, 30-4 and 30-5, which correction factor is associated with the specific sensor 8-1 through 8-5 that provided the reading. To calibrate the system 1, it is necessary to determine the correction factors 30-1 to 30-5 that need to be applied by the controller 3 in order to obtain the correct milk yield volumes from the readings 16-1 to 16-5 from each sensor 8-1 through 8-5. Instead of calibrating each of the sensors 8-1 through 8-5 manually or individually, in accordance with the present invention a different method is applied that enables to perform the calibration automatically.

The aggregate value D from calibrated milk meter 15, which is representative of the total quantity of milk D (or sometimes herein referred to as total milk yield D), may be used as a reference measurement to enable said automatic calibration of the other sensors 8-1 to 8-5. However, neither the application of a calibrated milk meter 15, nor the providing of a separate reference measurement, is an essential element of the invention. If a reference measurement is used, the function of providing the reference measurement may be implemented in an alternative manner than by using calibrated milk meter 15 of FIG. 1. For example, in an alternative embodiment, one or more of the sensors 8-1 to 8-5 may be accurately calibrated separately, such that the readings or measurements from these sensors 8 may be used as reference measurements. In fact, if only one of the sensors 8-1 to 8-5 is well calibrated, this obviated the need—for that purpose—for calibrated milk meter 15. As a further alternative, if at least one of the sensors 8-1 to 8-5 is indeed accurately calibrated separately, another possibility is to pre-set the correction factor of this calibrated sensor to 1.000 as a fixed value (or a different correction factor that may have been manually determined during or after calibration), and to mark this set correction factor as a calibrated or pre-set correction factor. The controller may then directly calculate the other correction factors based on the pre-set correction factor, without performing separate reference measurements.

Figure 2:
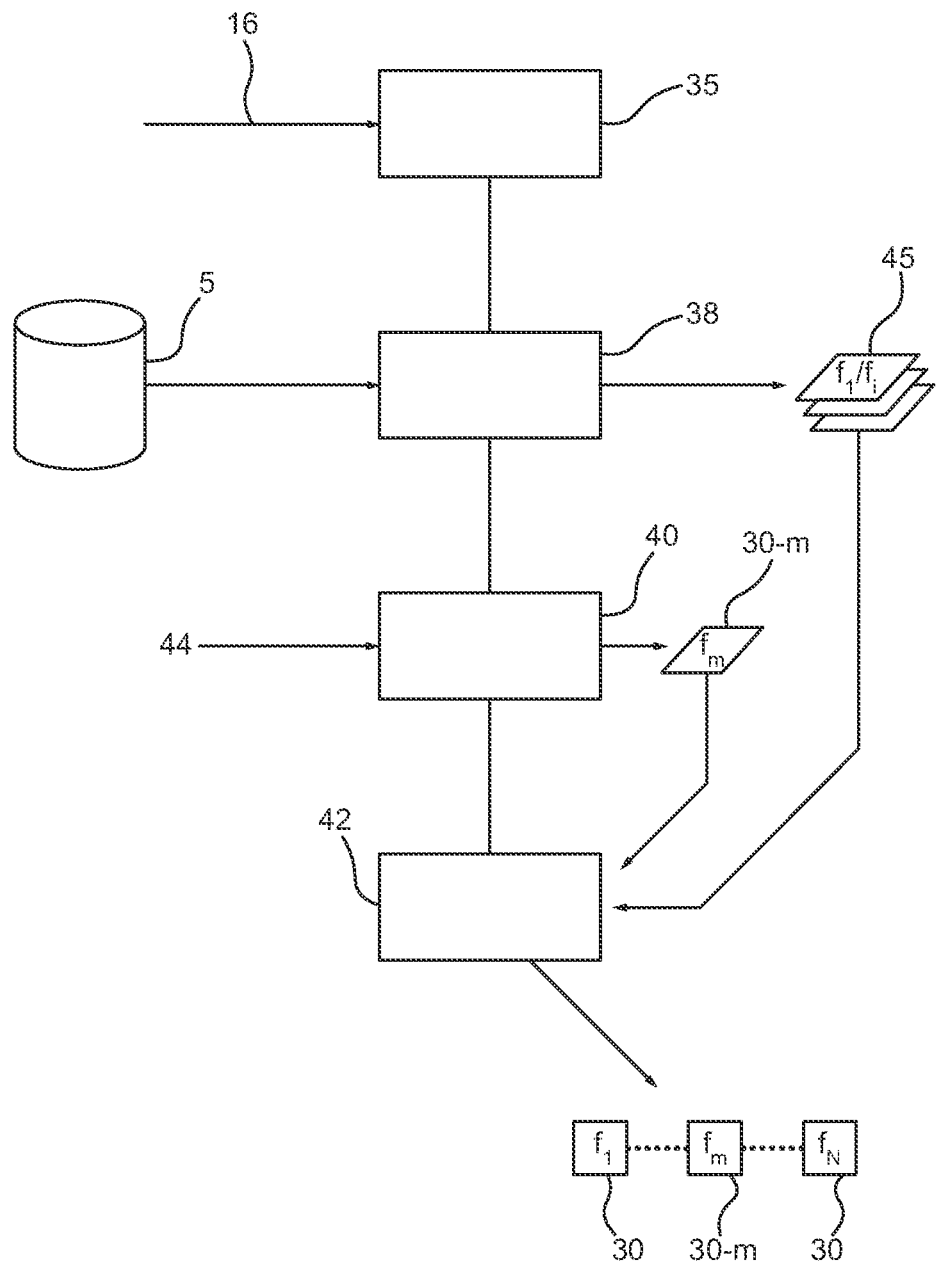
FIG. 2 schematically illustrates a method in accordance with an embodiment of the invention.

Turning to FIG. 2, the method of the present invention is schematically illustrated. To perform calibration, in accordance with an embodiment of the present invention in step 35, the sensor readings for a specific animal 10 with identifier k (element 11) are obtained as indicated by signal input 16. In step 35, also the sensor identifier that provided the sensor reading 16 for this animal is registered. This data may be stored in memory 5 (not indicated in FIG. 2). Then, in step 38, the controller 3 will access historic data from memory 5. From this historic data, the controller 3 may obtain a plurality of sensor readings for the animal 10 with identifier k obtained using different sensors over the period concerned. For example, in the system 1 of FIG. 1, for cow k, if the sensor reading 16 in step 35 was provided by sensor $S_1$ 8-1, then in step 38 the sensor reading from previous milking sessions will be obtained from the memory 5 which were taken with the sensors 8-2 through 8-5 (if available). In step 38, the sensor reading from step 35 will be divided by the sensor readings from the memory 5 obtained in step 38. Averages, a median, a percentile or a mode for each sensor of the sensor readings from the memory 5 obtained in step 38 may be used as a representative value for the sensor 8-2 to 8-5. This will provide a fraction 45 which is representative for each ratio between the correction factors $f_1$ of sensor $S_1$ 8-1 and each correction factor $f_i$ for sensor $S_i$ 8-i (where i=1 ... 5 in the system of FIG. 1). These fractions 45 are stored in memory 5. As suggested above, preferably but not essentially the calibration is performed on representative data. Therefore, statistical methods may be applied in order to make sure that the values used for sensor reading 16 and the measurements taken from memory 5 in step 38 are representative for each of these sensors, such as averages, a mode, or a median or a percentile for each of the measurements used in steps 35 and 38. This is not an essential feature and may be dispensed with, or may be implemented differently. Furthermore and also not essential and only in those cases where this may be of relevance, a correction may have to be performed on any sensor readings in order to compare these with each other. For example, for a milk meter, it may be desired to use a time corrected sensor reading (24 h milk yield or similar) before a comparison can be done. The sensor reading in step 35 may then be corrected by dividing it through the interval from the reading before. The sensor readings from the memory may also be divided by the interval between the reading and the one before. The timestamp may be stored in the memory, the interval or the calculated 24 h yield to perform this in a correct way. For example, reading/interval*24 h is may be used.

Next in step 40, preferably a reference measurement may be performed. This step will later be explained is FIGS. 3 and 4. The reference measurement 44 will be used to calculate in step 40 a representative correction factor $f_n$ 30-n for sensor $S_n$. Next in step 42, the fractions 45 calculated in step 38 and the correction factor 30-n calculated in step 40 are used to calculate all the other correction factors $f_1$ through $f_N$ 30.

As explained earlier above, each combination of sensors may be expressed as follows: $\delta_1/\delta_2 = f_2/f_1$, wherein $\delta_1$ and $\delta_2$ are measurement values obtained with respectively a first and second sensor, and wherein $f_1$ is the correction factor of the first sensor and $f_2$ is the correction factor of the second sensor. The fraction $\delta_1/\delta_2$ thus enables to calculate $f_2$, if $f_1$ can be found in another manner e.g. using a reference measurement or by calibrating one sensor and pre-setting a value. For example, if $\delta_{real}$ is the actual value of the animal related parameter to be determined (e.g. a quantity of milk in system 1), then $f_1 = \delta_{real}/\delta_1$, wherein $\delta_1$ is the sensor reading of the first sensor. With this information also $f_2$ can be calculated via: $f_2 = \delta_1 * f_1 / \delta_2$.

Figure 3:
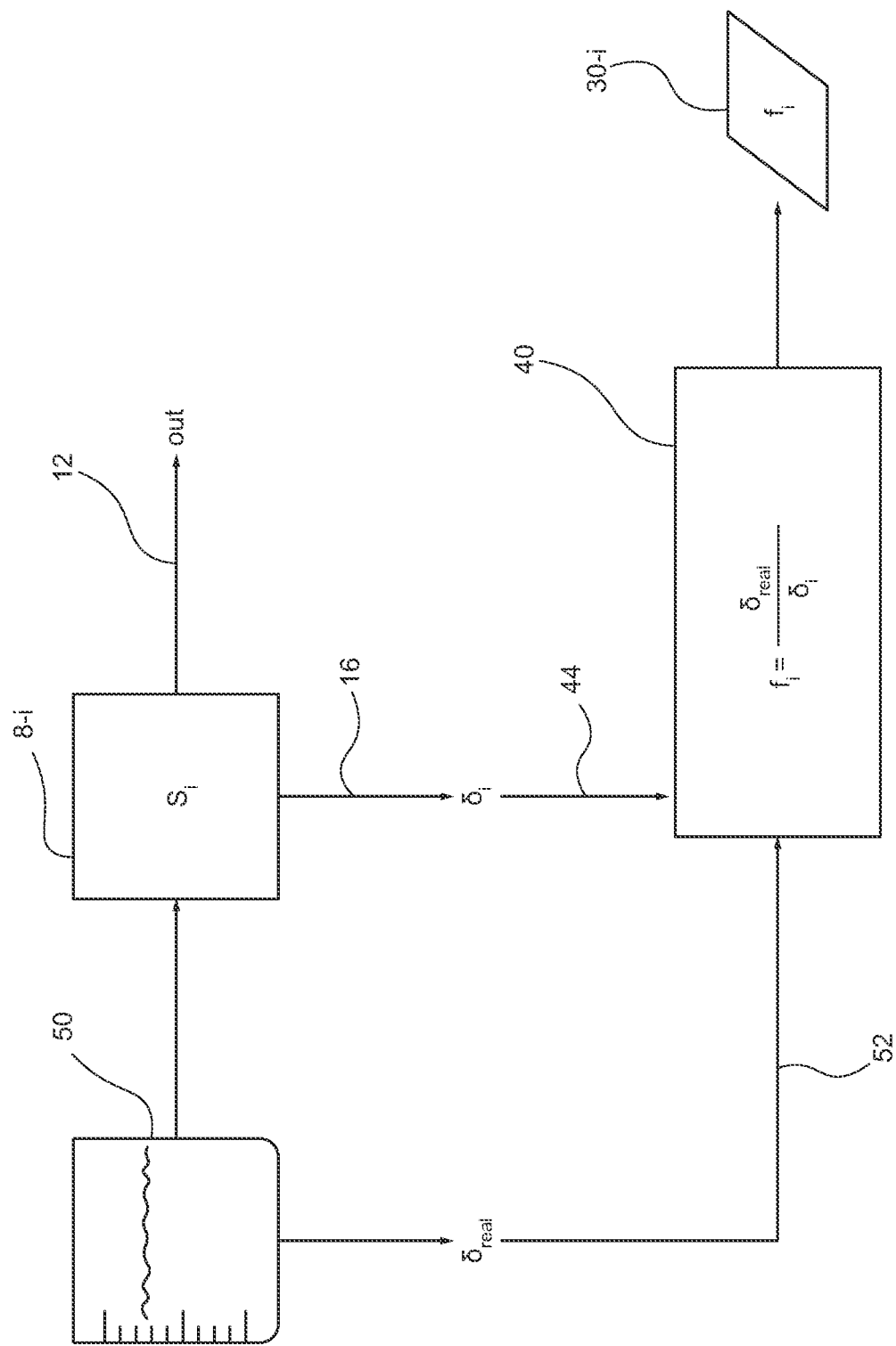
FIG. 3 schematically illustrates a step of obtaining a reference measurement for use in an embodiment of the invention.

FIG. 3 schematically illustrates one alternative implementation for performing a reference measurement and calculating a correction factor. In FIG. 3, the correction factor for sensor $S_1$ is calculated. For example, a known quantity of milk 50 may be provided to milk meter 8-i. After measuring the quantity 16 with the milk meter 8-i, the milk is provided to the milk outlet 12 of the milk meter 8-i. The reading of sensor $S_i$ is denoted as $\delta_i$ and is used as a reference measurement 44 in step 40. Because the real quantity of the milk 50 is known (for example using a calibrated milk meter of manually) this provides a calibrated value $\delta_{real}$ 52 that is provided to step 40. In step 40, the correction factor $f_i$ of sensor $S_i$ 8-i may be calculated directly from the input $\delta_{real}$ and $\delta_i$. The correction factor $f_i$ is illustrated as element 30-i of FIG. 3. Optionally, multiple measurements may be used from which a statistical representative value is chosen as the $f_i$ 30-i. This may be done to improve accuracy of the real correction factor.

Figure 4:
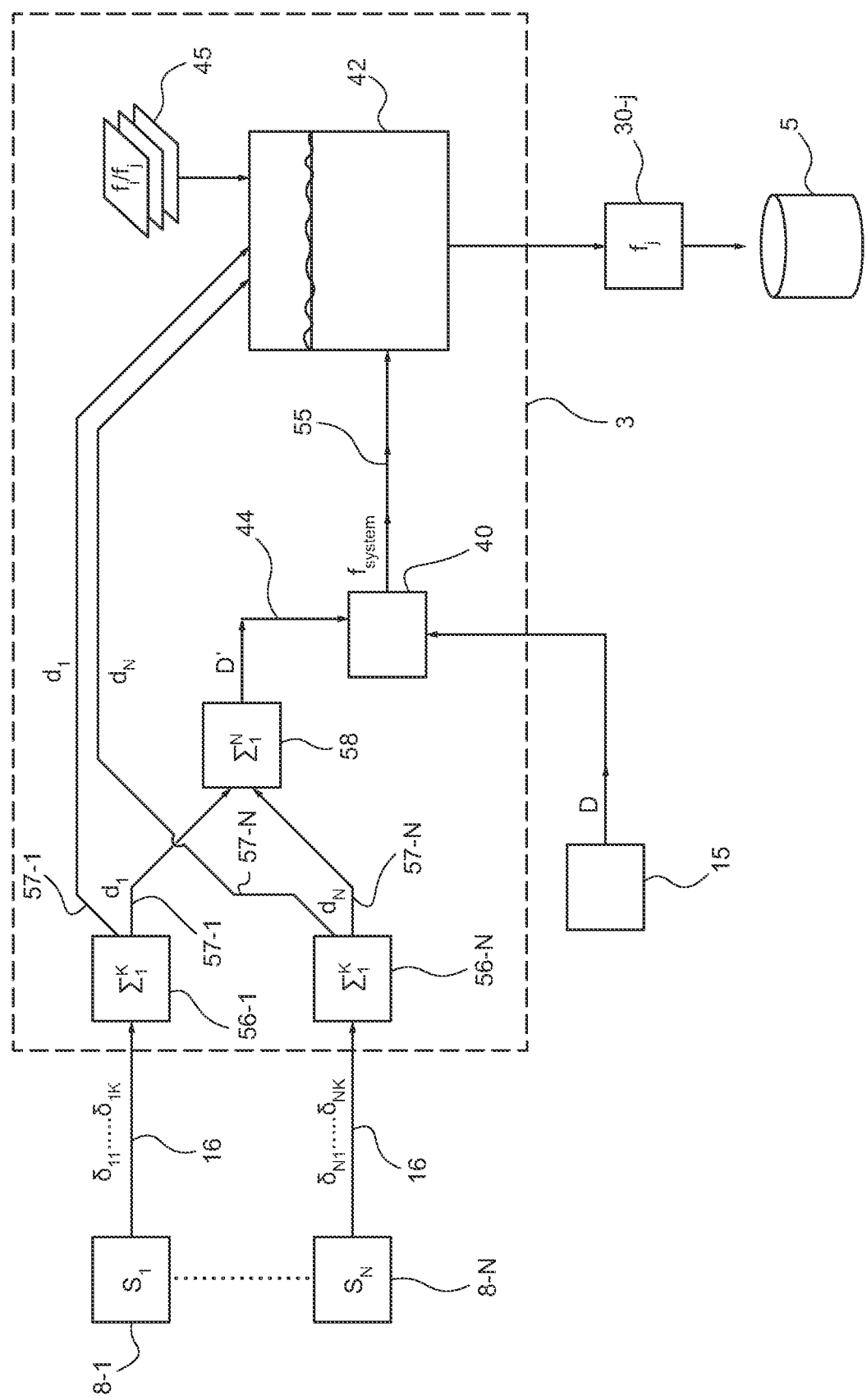
FIG. 4 schematically illustrates a step of obtaining a reference measurement for use in an embodiment of the invention.

FIG. 4 illustrates an alternative method to perform a reference measurement. This alternative method of FIG. 4 may be applied in the milk system 1 of FIG. 1. The milking system 1 of FIG. 1, however, is just one example of a system wherein the method of FIG. 4 may be applied. The method of FIG. 4 may likewise be applied in a different system, for example a system wherein transportation of other quantities is measured. To mention a typical example thereof, a feeding system wherein quantities of consumed feed are to be measured which are consumed by each individual animal of a group of animals may similarly apply a method as illustrated in FIG. 4 in order to perform a reference measurement automatically to allow automatic calibration. Using the example of FIG. 1, the method of FIG. 4 may be explained as follows.

Each of the $S_1$ through $S_n$ denoted by 8-1 through 8-N provides a plurality of individual quantities of milk obtained from a number of individual cows. The quantities measured by each of the sensors are denoted by $\delta_{ik}$, wherein i denotes the sensor number ranging from 1 to N, and wherein k denotes the cow number or cow identifier ranging from 1 to K. In the system of FIG. 1, there are five milk meters, so therefore N=5. Also, as mentioned, there are a total of seventy cows, so therefore K=70. During a single milking session, the cows arbitrarily visit one of the sensors $S_1$ through $S_5$ of FIG. 1, and therefore the milk quantities $\delta_{ik}$ provided by signal line 16 from each of the sensors 8-1 through 8-N will only include milk quantities from a subset of the animals 10 in the group. Therefore, in FIG. 4, for example for sensor $S_1$ 8-1, the reference to $\delta_{11} \ldots \delta_{1K}$ does not mean that sensor 1 provides the milk quantities $\delta$ for all cows in the group. Only the milk quantities of those cows that have visited the first sensor $S_1$ 8-1 are provided by sensor $S_1$ to the controller 3.

In calculations tabs 56-1 through 56-N, the milk quantities $\delta_{ik}$ for each of the sensors 8-1 through 8-N will be summed. This will provide the total sensor milk yields 57 denoted for each sensor $S_i$ by the letter $d_i$. Thus, for the sensors 8-1 through 8-N, this will provide the total sensor milk yields $d_1$ through $d_N$. The data symbol 57-1 through 57-N for $d_1$ through $d_N$ are provided to further summation step 58 in order to calculate the total measured milk yield D'. The quantity D' provides the total milk yield for all milk meters based on the measured quantities of the milk meters 8-1 through 8-N themselves, i.e. without being corrected by a correction factor 30-1 through 30-N.

In FIG. 1, an accurate and well calibrated milk meter 15 is present directly upstream of the milk storage tank 19. This milk meter 15 provides a calibrated reference for the total milk yield of all sensors together. This calibrated total milk yield provided by sensor 15 is denoted D. The quantity D provided by a sensor 15 and the measured total milk yield D' provided as in group 44 are provided to step 44, as illustrated in FIG. 4. In step 40, a correction factor of $f_{system}$ is calculated for the whole milking system 1 based on D and D'. Similar to calculating Lin FIG. 3, in step 40 of FIG. 4, $f_{system}$ is calculated by dividing D by D': $f_{system}=D/D'$. This system correction factor $f_{system}$ is provided as output 55 to step 42.

In step 42, the system correction value $f_{system}$ 55, the measured total sensor milk yields $d_1$ through $d_N$, and the fractions 45 obtained using the method of FIG. 2 are all used in order to calculate each individual correction factor $f_j$ (wherein j is an integer value between 1 and N, denoting the sensor number of the individual sensor with which the correction factor is associated). In FIG. 4, the correction $f_j$ is denoted by 30-j. Using the above mentioned inputs, these correction factors $f_j$ may be calculated by:

$$f_j = f_{system} \times \frac{\sum_i^N d_i}{\sum_i^N \left[d_i\left(\frac{f_i}{f_j}\right)\right]}$$

The correction factor $f_j$ may be stored in memory 5 for correcting the measurement values of each individual sensor $S_1$ through $S_N$ 8-1 through 8-N.

Figure 5:
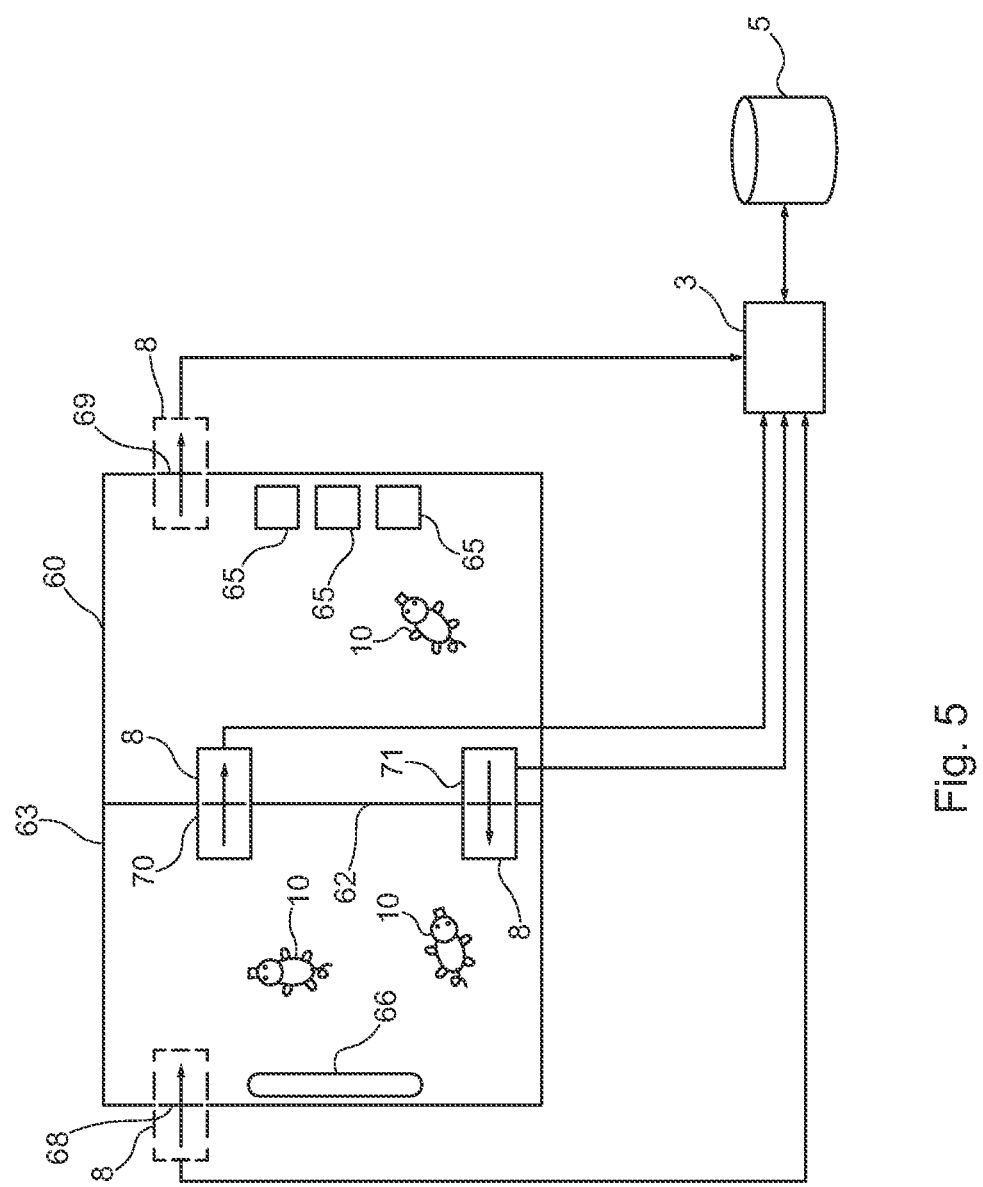
FIG. 5 schematically illustrates a training pen for gilts, including a weighing system wherein a method of the present invention is applied.

FIG. 5 illustrates an alternative system wherein the calibration of the present invention may be applied. In FIG. 5, a gilt training pen 60 is illustrated. The gilt training pen 60 comprises a fence 63 having an entrance 68 and an exit 69. Internally, the pen 60 is separated by a separation fence 62 which divides the pen 60 in two different areas. In the first area, the water system 66 provides water to the gilts 10. In the second area, a plurality of feeding systems 65 provided feed to the gilt 10. The gilts 10 may walk free between the first area and second area via the passages 70 and 71. In each of these passages 70 and 71, and optionally also in the entrance 68 and exit 69 to the pen 60, weighing units 8 may be present which enable to weigh each animal 10 passing through. Furthermore, each of the weighing units 8 also enables to identify the animal 10 passing through, for example by using RFID ear tags on the animals 10. The weight measurements from each of the weighing units 8 are provided to a controller 3, together with an animal identifier and such that the weighing unit 8 that performed the weighing can be identified. Furthermore, measured weights from each of the weighing units 8 is registered together with the identified animal number of animal 10 and the sensor number of the weighing unit 8 in memory 5. Typically, although the weights of the animals 10 varies slightly throughout the day due to consumption of food and excretion, the averages of these measured weights will only gradually change. Over the course of a couple of days, no drastic changes to the weight of each animal 10 is to be expected. Therefore, in the same way as in the milking system described here and before, the data from the weighing units 8, even though slide variations are present, more or less followed a trend. The data for weighing units 8 is therefore predictable.

Equivalent to the calibration of the milking system, representative values of the measured weights by each of the sensor units 8 may be obtained by for example averaging the measurements over the course of a couple of days, and calculating the fractions between the data from each sensor 8 with every other sensor in the system. This may be done based on the history data registered in the memory 5. A reference measurement to perform automatic calibration may be provided in various different ways, or may be dispensed with if one of the correction factors is made available in a different manner. For example, if one of the weighing units 8 is accurately calibrated, the correction factor for this weighing unit may be known, and the correction factor for all other weighing may be calculated as explained here and above. Alternatively or additionally, it is also possible to use an average over all weighing units 8 as a reference measurement. Although the latter may be slightly less accurate and slightly more prone to error, this may be convenient because no further reference measurements are then needed. This may be done, for example, if there is no bias in the devices. For the milk meter all correction factors f may be greater than 1, so a mean measurement will not provide a reliable reference measurement. However, if it would be known that on average a milk meter has a correction factor of f=1.10, then this information may be added and indeed an average measurement may be used. As a further alternative, the weights of one or more of the animals 10 may be obtained using a different calibrated scales, and the reference weight may be provided to the controller 3.

As explained above, although not illustrated in FIG. 5, the watering system 66 and each of the feeding stations 65 may likewise be part of one or more systems to which the calibration method of the present invention may be applied. Similar to a milking system such as system 1, the feeding system 65 or a watering system 66 can be used to measure quantities associated with individual animals. Although the milking system 1 measures quantities of milk provided by each animal 10 and gathered in a storage tank 19, the feeding system 65 provides quantities of feed to each individual animal 10, which can be measured by individual sensors in each feeding station 65. The same is true for a watering system 66. In addition to the above mentioned example, the method of the present invention may be applied to other farming systems that perform measurements amongst a group of animals 10, associated with individual animals thereof. The present invention is not limited to application in the above mentioned examples only.

In the above, amongst others, the calculation of representative values 45 for each ratio between the correction factors $f_1$ of sensor $S_1$ 8-1 and each correction factor $f_i$ for sensor $S_i$ 8-i (where i=1 ... 5 in the system of FIG. 1) has been discussed as example. It is to be understood that an optional additional step to this may be to perform a further processing step wherein these values 45 are evaluated and—where desired—corrected in order to make them consistent. In principle, the fractions for each combination of sensors in total may be set in a matrix, which matrix should form a consistent and reciprocal matrix. On it's diagonal, the values are equal to 1 by definition (as it provides the fractions of each sensor with respect to itself). Off the diagonal, the values above and below the diagonal must be consistent in that e.g. $f_2/f_1$ must be the reciprocal of $f_1/f_2$. Furthermore, $(f_i/f_j) \times (f_j/f_k) = (f_i/f_k)$ must be valid. In those cases where discrepancies are found, the matrix may be made consistent again. This can be done by weighing or penalizing the values dependent on their consistency.

One of these manners of making the matrix consistent again applies theorem five of Benitez. Given a reciprocal matrix A, the method finds the consistent matrix Y for which a certain distance (defined by the Frobenius norm of the difference between log(A) and log(Y)) is minimized (see theorem 2 of Benitez). For this matrix Y, the off-diagonal elements are modified such that they are consistent.

Another manner is based on statistical principles. The accuracy of the statistically representative fractions are given by the errors on such values. For example, the error on a mean value is given by the standard deviation (std) divided by the square root of the number of measurements used:

Error on mean$(fi/fj)=std(fi/fj)/\sqrt{N}$.

To fine-tune the statistically representative ratios such that they become consistent with each other, one may apply the freedom available for each value to adapt them. Thus, besides the statically representative ratios fi/fj (e.g. mean or median) also the standard deviation needs to be calculated. If a fraction from a trial solution deviates more than the 'error on the mean' from the original median fraction observed, then this trial solution may be more penalized than a solution which remains relatively close to the median ratios observed. Similarly, penalties may be given to ratios that are not consistent with each other. If the multiplication of the trial ratios of $(f_i/f_j)$ and $(f_j/f_k)$ does not equal $(f_i/f_k)$, then a penalty will be given. More penalty points may be given if the deviation is greater. In the end, the trial solution for which the fractions result in the least penalty points, may be denoted as the best or most consistent solution.

In addition, a brute force method, Markov Chain Monte Carlo modelling, or any other fitting/optimizing modules can be used to search for the most consistent solution.

The present invention has been described in terms of some specific embodiments thereof. It will be appreciated that the embodiments shown in the drawings and described herein are intended for illustrated purposes only and are not by any manner or means intended to be restrictive on the invention. The context of the invention discussed here is merely restricted by the scope of the appended claims.

What is claimed is:

1. A method for calibrating a plurality of sensors in a system for obtaining animal data from a group of animals, wherein the plurality of sensors are configured to obtain measurements of an animal related parameter, wherein for obtaining the measurements the system is configured for allowing each animal to arbitrary visit one of the sensors, and wherein the method comprises:
obtaining, for at least one animal of the group of animals, a first measurement associated with a first sensor of the plurality of sensors;
calculating one or more relations between the first measurement and one or more second measurements associated with the respective animal, wherein each of the second measurements is obtained using one of a further sensor of the plurality of sensors, wherein the one of the further sensors is different from the first sensor, so as to obtain at least one representative relation for each combination of the first sensor and each one of the further sensors; and
calculating based on the at least one representative relation, a correction parameter associated with at least one sensor of the plurality of sensors, for harmonizing an output signal of the at least one sensor with respect to output signals of one or more of the further sensors of the plurality of sensors.

2. The method according to claim 1, wherein the correction parameter is at least one of the group consisting of: a correction factor, and an offset.

3. The method according to claim 1, wherein the correction parameter is a correction factor, and
wherein the calculating one or more relations comprises calculating one or more fractions between the first measurement and one or more second measurements, so as to obtain at least one representative fraction for each combination of the first sensor and each one of the further sensors.

4. The method according to claim 1, wherein the second measurements are obtained from a data repository containing measurement data of earlier measurements,
wherein, in the measurement data, each measurement is associated with an animal identifier of an animal from the group of animals, and
wherein, in the measurement data, each measurement is associated with a sensor identifier of the sensor with which the measurement has been obtained.

5. The method according to claim 1, wherein the first measurement is obtained by at least one of the group consisting of:
obtaining the first measurement from a data repository containing measurement data of earlier measurements; and
directly obtaining the first measurement from the first sensor.

6. The method according to claim 1, wherein the one or more second measurements include at least one of the group consisting of:
at least one measurement from each of the sensors different from the first sensor; and
a plurality of measurements from one or more of each of the further sensors, and
wherein the calculating one or more relations is performed by calculating relations between the first measurement and a statistical representative value of the plurality of measurements for each of the further sensors.

7. The method according to claim 6, wherein the one or more second measurements include a plurality of measurements from one or more of the further sensors,
wherein the calculating one or more relations is performed by calculating relations between the first measurement and a statistical representative value of the plurality of measurements for each of the one or more of the further sensors, and
wherein the statistical representative value is at least one of: an average; a median value; a mode; or a percentile of the plurality of measurements of the further sensor.

8. The method according to claim 1, wherein for obtaining the at least one representative relation for each combination of the first sensor and each one of the further sensors, the method further comprises:
storing, after the calculating one or more relations, each of the calculated relations in a data repository; and selecting from the data repository, for each combination, a plurality of stored relations and calculating the representative relation from the selected plurality of stored relations.

9. The method according to claim 8, wherein the selecting a plurality of stored relations and calculating the representative relation comprises obtaining, with respect to the stored relations or the selected relations, at least one of the group consisting of: an average; a median value; a mode; and a percentile.

10. The method according to claim 1, wherein the method further comprises modifying one or more of the at least one representative relation within of a set containing representative relations of each combination of the first sensor and each one of the further sensors,
wherein the modifying includes correcting the one or more representative relations so as to bring the representative relations in conformity with each other.

11. The method according to claim 1, wherein the method further comprises:
obtaining a reference measurement of the at least one animal related parameter using at least one sensor of the plurality of sensors; and
wherein, in addition to the at least one representative relation, the correction parameter is calculated based on the reference measurement.

12. The method according to claim 11, wherein the reference measurement comprises one or more measurements of the at least one animal related parameter obtained using a reference sensor, wherein the reference sensor is at least one of:
an arbitrary sensor of the plurality of sensors; and
a calibrated sensor.

13. The method according to claim 11, further comprising:
calculating, for the reference sensor, a correction parameter based on the reference measurement and a calibrated value, wherein the calibrated value is a representative value for the at least one animal related parameter; and
calculating, based on the correction parameter of the reference sensor and the at least one relation for each combination of the first sensor and each one of the further sensors, further correction parameters, so as to obtain correction parameters for each sensor of the plurality of sensors.

14. The method according to claim 1, wherein the first measurement and the one or more second measurements are obtained within a predefined time period, such that within the predefined time period the obtained measurements of the animal related parameter are correlated in accordance with a data trend.

15. The method according to claim 14, wherein the first measurement is obtained at a first moment of time and the second measurement is obtained at a second moment of time, wherein prior to performing the calculating the one or more relations between the first measurement and one or more second measurements, the method includes:
dividing the first measurement by a first calculated estimate and dividing the second measurement by a second calculated estimate, wherein the first calculated estimate and the second calculated estimate are determined based on the data trend.

16. The method according to claim 15, wherein the data trend is determined based on measurements performed using one or more sensors of the plurality of sensors.

17. The method according to claim 1, further comprising filtering the one or more second measurements, wherein the filtering is performed using at least one criterion taken from the group consisting of:
excluding second measurements from the one or more second measurements for which a measurement result pertains to a statistical outlier; and
excluding second measurements from the one or more second measurements dependent on a status of the at least one animal.

18. The method according to claim 1, wherein the correction parameter includes both a correction factor and an offset, and
wherein the correction factor and the offset are obtained, for each of the plurality of sensors, by fitting.

19. The method according to claim 1, wherein for each one of the one or more of the first measurement and the further measurements, the measurement is obtained within an associated time interval following a preceding measurement, and
wherein the one or more of the first measurement and the further measurements are modified to correct for the associated time intervals.

20. The method according to claim 1, wherein the system for obtaining animal data from a group of animals is a milking system for milking animals of the group of animals,
wherein the animals are dairy animals,
wherein the sensors of the plurality of sensors comprise at least one element of the group consisting of:
a milk meter wherein the measurements comprise measurements of quantities of milk obtained from each of the animals;
a conductivity sensor for determining a conductivity of the milk obtained,
a color meter for determining a color of the milk obtained,
a fat percentage sensor,
a protein sensor for determining a specific amount of protein in the milk obtained,
a cell count sensor for determining a somatic cell count of the milk, and
a lactose sensor for determining a lactose level of the milk.

21. The method according to claim 20, wherein the correction parameter is a correction factor,
wherein the sensors of the plurality of sensors comprise milk meters,
wherein the measurements comprise measurements of quantities of milk obtained from each of the animals, and
wherein the method further comprises obtaining a reference measurement of the at least one animal related parameter using at least one sensor of the plurality of sensors, and wherein in addition to the at least one representative relation, the correction factor is calculated based on the reference measurement; wherein the milking system comprises N milk meters, and
wherein the obtaining the reference measurement comprises:
obtaining a total milk yield D from all milk meters in the system during at least one complete milking session;
obtaining a sensor milk yield $d_i$ representative of a total milk yield of an $i^{th}$ milk meter during the at least one complete milking session, wherein $1 \leq i \leq N$ and $i \in N$;
calculating a system correction factor $f_{system}$ as:

$$f_{system} = \frac{D}{\sum_{i=1}^{N} d_i};$$

and
wherein the calculating the correction factor for a $j^{th}$ milk meter, wherein $1 \leq j \leq N$ and $j \in N$ and $j \neq i$, comprises calculating $f_j$ as:

$$f_j = f_{system} \times \frac{\sum_{i}^{N} d_i}{\sum_{i}^{N}\left[d_i\left(\frac{f_i}{f_j}\right)\right]}.$$

22. The method according to claim 1, wherein the system for obtaining animal data from a group of animals is a weighing system,
wherein the sensors of the plurality of sensors are weighing units, and
wherein the measurements comprise measurements of weights of individual animals from the group of animals.

23. The method according to claim 22, wherein the method further comprises obtaining a reference measurement of the at least one animal related parameter using at least one sensor of the plurality of sensors, and
wherein in addition to the at least one representative relation, the correction parameter is calculated based on the reference measurement, wherein the reference measurement comprises:
an average weight of an individual animal obtained by averaging measurements of weights of the respective animal obtained using at least a subset of the sensors, including at least two of the sensors.

24. The method according to claim 1, wherein the system for obtaining animal data from a group of animals is a feeding system comprising one or more feeding stations,
wherein the sensors of the plurality of sensors are weighing units for determining a quantity of feed, and
wherein the measurements comprise measurements of quantities of feed consumed by individual animals from the group of animals.

25. The method according to claim 1, wherein the system for obtaining animal data from a group of animals is a measuring system wherein the sensors of the plurality of sensors are configured for measuring animal related parameters including at least one element of the group consisting of: temperature; color; size; mobility, and behavioral parameters.

26. A non-transitory computer-readable medium including computer-executable instructions that, when executed by a processor, facilitate carrying out a method in a system for obtaining animal data from a group of animals, for calibrating a plurality of sensors of the system, wherein the sensors are configured to obtain measurements of an animal related parameter, wherein for obtaining the measurements the system is configured for allowing each animal to arbitrary visit one of the sensors, wherein the method comprises:
obtaining, for at least one animal of the group of animals, a first measurement associated with a first sensor of the plurality of sensors;
calculating one or more relations between the first measurement and one or more second measurements associated with the respective animal, wherein each of the second measurements is obtained using one of a further sensor of the plurality of sensors, wherein the one of the further sensors is different from the first sensor, so as to obtain at least one representative relation for each combination of the first sensor and each one of the further sensors;
obtaining a reference measurement of the at least one animal related parameter using at least one sensor of the plurality of sensors; and
calculating, based on the reference measurement and the at least one representative relation, a correction parameter associated with at least one sensor of the plurality of sensors, for harmonizing an output signal of the at least one sensor with respect to output signals of one or more of the further sensors of the plurality of sensors.

* * * * *